(12) United States Patent
Zhang et al.

(10) Patent No.: US 6,641,846 B2
(45) Date of Patent: Nov. 4, 2003

(54) PHARMACEUTICAL COMPOSITION AGAINST TYPE I ALLERGY AND THE PREPARATION THEREOF

(75) Inventors: Zuoguang Zhang, Beijing (CN); Yanling Fu, Beijing (CN)

(73) Assignee: Tianjin Yanling Health Food Co., Beijing (CN)

( * ) Notice: Subject to any disclaimer, the term of this patent is extended or adjusted under 35 U.S.C. 154(b) by 138 days.

(21) Appl. No.: 09/761,055

(22) Filed: Jan. 16, 2001

(65) Prior Publication Data

US 2002/0090402 A1 Jul. 11, 2002

(30) Foreign Application Priority Data

Nov. 8, 2000 (CN) ........................................ 00133485 A

(51) Int. Cl.[7] ................................................. A61K 35/78
(52) U.S. Cl. ....................... 424/725; 424/439; 424/728; 424/729; 424/739; 424/741; 424/756; 514/2
(58) Field of Search ................. 424/725, 439, 424/728, 729, 739, 741, 756; 514/2

(56) References Cited

FOREIGN PATENT DOCUMENTS

| CN | 1230432 | * | 10/1999 |
| JP | 1161219 | * | 7/1986 |
| JP | 63027435 | * | 2/1988 |
| JP | 40110202 | * | 4/1989 |
| JP | 01180822 | * | 7/1989 |
| JP | 02290812 | * | 11/1990 |
| JP | 06279305 | * | 10/1994 |
| JP | 2609562 | * | 5/1997 |
| JP | 10218784 | * | 8/1998 |
| SU | 1806747 | * | 2/1990 |

OTHER PUBLICATIONS

Yagi et al. Yakugaku Zasshi (1981), 101 (8): 700–7. Studies on the constituents of Zizyphi frucuts. IV. Isolation of an antiallergic component, ethyl alpha–D–fructfuranosided from ethanol extract of Zizyphi fructus.*

Cyong, JC. Acupunct Electro–Ther Res. (1981), 6(4): 285–302. Purification and identification of cyclic nucleotides in Oriental medicinal herbs.*

Yunde et al. Chinese Medical J (1981), 94 (1): 35–40. Effect of Radix Astragali Seu Hedysari on the interferon system.*

Starokozhko, L.E. Vestnik Dermatologii i Vernerologii (1996), vol. 0, No. 2: 34–37. Radix glychyrrhizae foam system of drug delivery in dermatologic practice.*

Starokozhko, L.E. Vestnik Dermatologii i Vernerologii (1995), vol. 0, No. 5: 14–17. New medicines for external usage from radix glycyrrhizae.*

Yamahara et al. Yakugaku Zasshi (1982), 102(9): 881–886. Biologically active principles of crude drugs antiallergic principles of Shoseiryo–To– 1. Effect on delated type allergy reaction.*

* cited by examiner

Primary Examiner—Christopher R. Tate
Assistant Examiner—Michele C. Flood
(74) Attorney, Agent, or Firm—Morrison & Foerster LLP

(57) ABSTRACT

The invention is related to a pharmaceutical composition with its main effects against Type I Allergy and the process thereof. The composition mainly comprises the following raw materials by weight ratio: 30~60 parts of *Fructus Jujubae*, 12~55 parts of *Radix Astragali*, 8~15 parts of Radix glycyrrhizae, 6~12 parts of *Ramulus cinnamomi*, 6~12 parts of Ginger and 4~8 parts of Green tea.

19 Claims, 1 Drawing Sheet

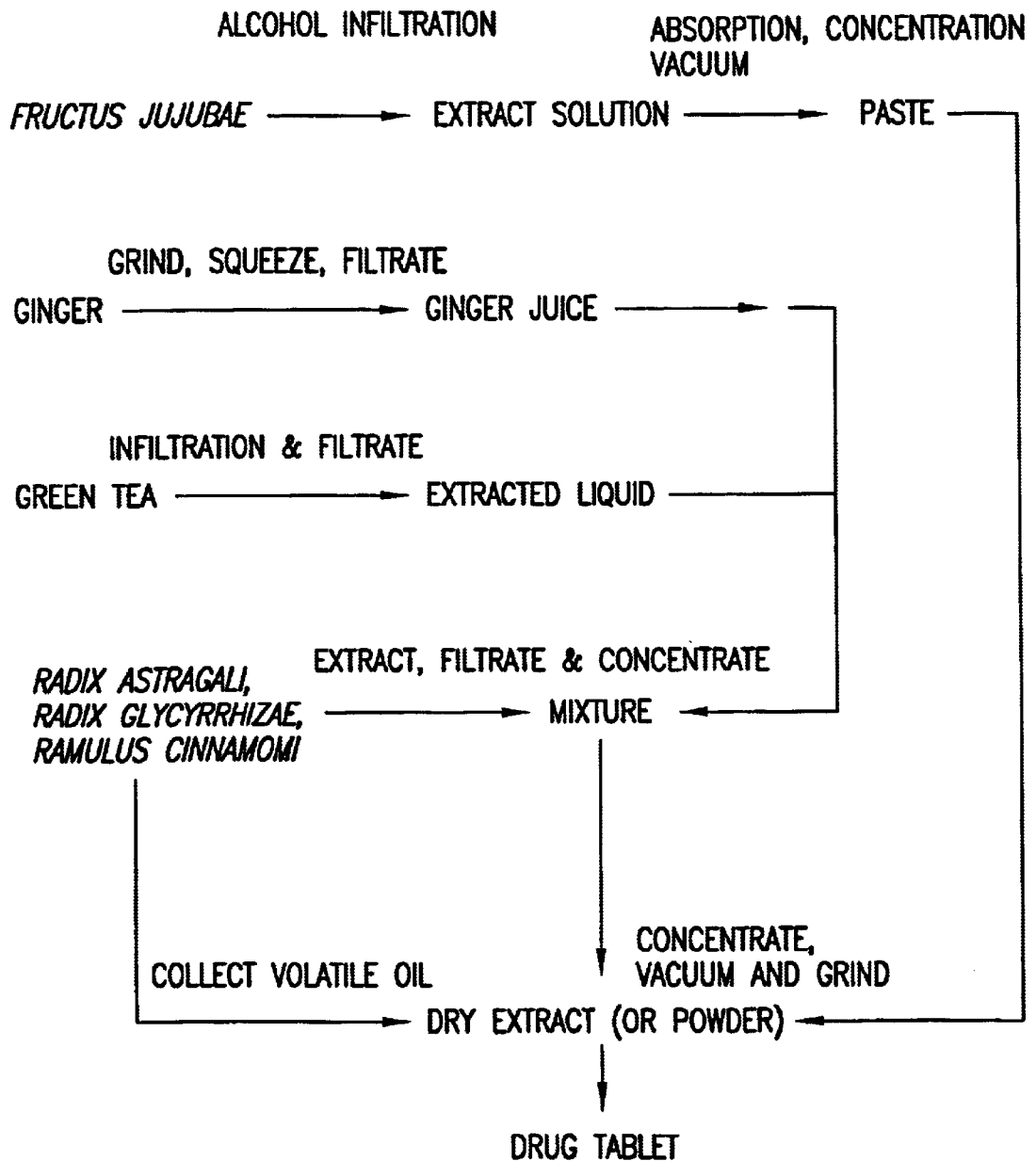

PHARMACEUTICAL COMPOSITION AGAINST TYPE I ALLERGY AND THE PREPARATION THEREOF

FIELD OF THE INVENTION

This invention is related to a pharmaceutical composition with its main effect against Type I Allergy, especially to one medicament with anti-allergic effect, which can also be used as an immune regulator.

This invention is also related to a method of a pharmaceutical composition with its main effect against Type I Allergy.

BACKGROUND OF THE INVENTION

Allergic diseases are common ones that harm human health seriously. Especially with the pollution of living environment of human beings and the changed dietary structures, patients suffering from allergic diseases are increasing rapidly. In an article in the American newspaper, "Medical Forum", of Jan. 12, 2000, it was reported that "there are about 38% of Americans who suffer from some types of allergic diseases". Additionally, according to some related statistical materials, in the world, there are about 700-800 millions of people who suffer from allergic diseases, among whom the patients suffering from Type I Allergy amount to quite a great proportion. Type I Allergy is a reaction that occurs rapidly when human makes contact again with its allergic antigen. In clinical cases, it is common that the allergic diseases are allergic asthma, allergic rhinitis, allergic dermatitis, allergic gastroenteritis, etc. Serious allergic diseases can even cause patients to go into shock. The pathogenesis of Type I Allergy is that the antigen-antibody reaction occurs on the surface of mastocytes. Said mastocytes are following to be damaged and cAMP in cell plasma is reduced with increased cGMP and penetrability of cell membrane is changed, so that it rapidly releases allergic active mediums, such as histamine, 5-hydroxytryptamine (5-HT), bradykinin or slowly reactive materials and the like.

In the modern medical researches, it is proven that regulation of human cAMP, cGMP and IgE can inhibit and take precautions against Type I Allergy effectively to prevent from releasing allergic mediums and reducing the reaction from local inflammation reaction of target cells. But in the Chinese traditional medicine theory, it is thought that it occurs due to general debility in three internal organs of lung, spleen and kidney, which leads to pathological changes such as deficiency and lack of vital energy, turbid asthma, etc. And allergic diseases would occur easily under external unhealthy conditions.

At present, anti-histamine and anti-allergic inhibitors as medicament are taken to cure allergy. But the effects of these medicines known in the arts only remain for a short time with a lot of side effect to a different degree, so that people cannot take them for a long time. People can only take said medicament in allergic occurrence to relieve the symptoms of allergic reactions locally. But it is difficult to improve allergic constitution, inhibit and prevent from allergic reactions through regulating human immune functions. With Chinese medicines, allergic diseases can be cured according to their symptoms by means of counteraction and harmonization and building up human resistance to diseases. Although Chinese Medicaments have good immune regulative effects, doctors of traditional Chinese medicine have not taken allergy as one independent course of study and made researches on it. Up to now, they have not combined the research results in incidence pathogenesis of allergy, which are obtained in modern medicines, with traditional herb prescriptions that can cure allergic diseases. The traditional medical doctors have not begun correcting allergic constitution to inhibit and prevent from allergic diseases by means of effective regulation of human cAMP/cGMP and IgE.

In order to overcome deficiency of the prior arts, the object of this invention is to provide one pharmaceutical composition with its main effects against Type I Allergy, especially herb medicament.

The present pharmaceutical composition is prepared with purely natural plants or herbs as its raw materials without any side effects and can inhibit and prevent Type I Allergy by means of regulation of human cAMP/cGMP. It can be used as an anti-allergic immune regulator that can be taken for a long time.

Another object of this invention is to provide a preparation method of the above-mentioned pharmaceutical composition with its main effects against Type I Allergy.

SUMMARY OF THE INVENTION

According to the present invention, the said medicament is prepared with purely natural herbs as its raw materials that can be taken as medicaments or as food. Such medicament has no side effects and can regulate immune functions of human body, harmonize allergic constitution of patients, inhibit and prevent human Allergy.

The embodiment of this invented medicament is based on the knowledge and pathogenesis of incidence of allergic diseases in traditional Chinese medicine in combination of the research achievements in the modern medicine and pharmacology. By use of pharmacologically acceptable active herb with function of immune regulation, the anti-allergic effects of the traditional Chinese herb medicines are strengthened and optimized, especially, this immune regulator not only can be taken for a long time to prevent incidence of allergic diseases through correcting allergic constitution of patient, but also can cure symptoms of allergic diseases effectively by their incidence.

In order to achieve the object of this invention, the following technical embodiments are taken for the present invention:

As mentioned above, this invention refers especially to a pharmaceutical composition with its main effects against Type I Allergy. In the invention, common jujube fruit (*Fructus Jujubae*) is used in fresh or dried one. It is a fruit of *Ziziphus jujuba* Mill. Membranous milk vetch root (*Radix Astragali*), a root of herb called *Astragalus membranaceus* (Fisch.) Bge. or *Astragalus membranaceus* (Fisch.) Bge. Var. mongholicus Bge. Hsiao and ural Licorice root (*Radix glycyrrhizae*), a root of herb called *Glycyrrhiza uralensis* Fisch., Cassiabarktree branchlet (*Ramulus cinnamomi*), Ginger and Green tea are also used as raw material for the herb medicament.

A herb medicament or pharmaceutical composition is prepared as the raw materials in accordance with the following weight ratio:

| | |
|---|---|
| *Fructus Jujubae* | 30 ~ 60 parts |
| *Radix Astragali* | 12 ~ 55 parts |
| *Radix glycyrrhizae* | 8 ~ 15 parts |
| *Ramulus cinnamomi* | 6 ~ 12 parts |

-continued

|  |  |
|---|---|
| Ginger | 6 ~ 12 parts |
| Green tea | 4 ~ 8 parts |

The preferred prescription of this pharmaceutical composition is prepared with the raw materials in accordance with the following weight ratio:

|  |  |
|---|---|
| Fructus Jujubae | 35 ~ 55 parts |
| Radix Astragali | 15 ~ 50 parts |
| Radix glycyrrhizae | 8 ~ 12 parts |
| Ramulus cinnamomi | 6 ~ 10 parts |
| Ginger | 6 ~ 10 parts |
| Green tea | 5 ~ 7 parts |

The most preferred prescription of this pharmaceutical composition is prepared as raw materials in accordance with the following weight ratio:

|  |  |
|---|---|
| Fructus Jujubae | 50 parts |
| Radix Astragali | 30 parts |
| Radix glycyrrhizae | 10 parts |
| Ramulus cinnamomi | 8 parts |
| Ginger | 8 parts |
| Green tea | 6 parts |

In the above-mentioned pharmaceutical composition with its main effects against Type I Allergy, optionally, common peony root, the root of herbaceous peony (*Radix Paeoniae Alba*)(10 20 parts) and/or Baikal skullcap root (*Radix scutellariae*) (10-20 parts) can also be added to strengthen its anti-allergic effects further.

The pharmaceutical composition mentioned in this invention contains pharmaceutically acceptable additives. And the mentioned medicament can be made to form any type of drug described in pharmacy, preferably drug in form of powder or tablet.

This invention is also related to an extract of the pharmaceutical composition with its main effects against Type I Allergy. The said extract is obtained with the following steps:

1. 30~60 weight parts of *Fructus Jujubae* are putted into a warm alcohol solution and keeping its pH value between 3.6~3.8. After it is extracted and filtered, the extract solution is obtained. Then, the said extract solution is absorbed several times with macro porous resin for eliminating sugar. After concentrating and drying in vacuum, the dried extract of *Fructus Jujubae* is obtained.
2. 6~12 weight parts of ginger are squeezed and filtered with a plate frame filter. The extracted liquid of ginger is obtained.
3. 4~8 weight parts of green tea are infiltrated into boiled water and filter them with a plate frame filter. The extracted liquid of green tea is obtained.
4. 15~55 weight parts of *Ramulus cinnamomi*, 8~15 weight parts of *Radix glycyrrhizae*, 6-12 parts of *Ramulus cinnamomi* are mixed together and decocted. The volatile oil of mixture is collected. After mixture is filtered, the mixed extracted liquid is obtained.
5. The said mixed extracted liquid obtained in step 4 is mixed and concentrated with the extracted liquid of green tea. Then, above extracted liquid of ginger is added and concentrated continuously until it reaches the relative density of 1.1~1.4/80~85° C. Then, one thick paste is obtained and followed by vacuuming it into a dry extract.
6. The dry extract obtained in step 5 is grinded and mixed with the dry extract of *Fructus Jujubae* obtained in step 1. The extract of this invention is obtained.

In the above-mentioned extraction method, preferably the extract is prepared with the materials in accordance with the following weight ratio:

|  |  |
|---|---|
| Fructus Jujubae | 35 ~ 55 parts |
| Radix Astragali | 15 ~ 50 parts |
| Radix glycyrrhizae | 8 ~ 12 parts |
| Ramulus cinnamomi | 6 ~ 10 parts |
| Ginger | 6 ~ 10 parts |
| Green tea | 5 ~ 7 parts |

In addition, in the above-mentioned extraction method, it is most preferable that the extractive is prepared with the materials in accordance with the following weight ratio:

|  |  |
|---|---|
| Fructus Jujubae | 50 parts |
| Radix Astragali | 30 parts |
| Radix glycyrrhizae | 10 parts |
| Ramulus cinnamomi | 8 parts |
| Ginger | 8 parts |
| Green tea | 6 parts |

In the above-mentioned extraction method, optionally, common peony root, the root of herbaceous peony (*Radix Paeoniae Alba*) (10~20 parts) and/or Baikal skullcap root (*Radix scutellariae*) (10~20 parts) can also be added to strengthen its anti-allergic effects further.

The above-mentioned extract can be processed into any form of a drug described in the pharmacy. In the above-mentioned extract, it can contain the pharmaceutically acceptable additives.

In addition, this invention refers also to one method for a pharmaceutical composition with its main effects against Type I Allergy. This method comprises the following steps:

1. 30~60 weight parts of *Fructus Jujubae* are putted into a warm alcohol solution and keeping its pH value between 3.6~3.8. After it is extracted and filtered, the extract solution is obtained. Then, the said extract solution is absorbed several times with macro porous resin for eliminating sugar. After concentrating and drying in vacuum, the dried extract of *Fructus Jujubae* is obtained.
2. 6~12 weight parts of ginger are squeezed and filtered with a plate frame filter. The extracted liquid of ginger is obtained.
3. 4~8 weight parts of green tea are infiltrated into boiled water and filter them with a plate frame filter. The extracted liquid of green tea is obtained.
4. 15~55 weight parts of *Ramulus cinnamomi*, 8~15 weight parts of Radix glycyrrhizae, 6~12 parts of *Ramulus cinnamomi* are mixed together and decocted. The volatile oil of mixture is collected. After mixture is filtered, the mixed extracted liquid is obtained.
5. The said mixed extracted liquid obtained in step 4 is mixed and concentrated with the extracted liquid of green tea. Then, above extracted liquid of ginger is added and concentrated continuously until it reaches the relative density of 1.1~1.4/80~85° C. Then, one thick paste is obtained and followed by vacuuming it into a dry extract.
6. The dry extract obtained in step 5 is grinded and mixed with the dry extract of *Fructus Jujubae* obtained in step 1. The extract of this invention is obtained.

In the above-mentioned method, Furthermore, optionally, common peony root, the root of herbaceous peony (*Radix Paeoniae Alba*)(10~20 parts) and/or Baikal skullcap root (*Radix scutellariae*) (10~20 parts) can also be added in step 4 to strengthen its anti-allergic effects further.

According to the invention, the said pharmaceutical composition and the extract can also be used to produce health food or food additives.

The composition or extract of this invention have the following features and advantages:

As an anti-allergic immune regulator, this pharmaceutical composition or extract have the preventive and curing dual functions against Type I Allergy without toxic side effects. When it is taken over a long period of time, it can correct allergic constitution and strengthen human immunity.

1. All the raw materials selected for the preparation of this pharmaceutical composition or extract of this invention are the natural edible plants that can be taken not only as food, but also as medicines. All the parts of the components comply with the "Regulations of Health Food Management" and the "Law of Drug" of the People's Republic of China. And it does not have toxic side effects. Man can take it over a long period of time.
2. With this pharmaceutical composition or extract of this invention, the present common method that a medicament is taken for treatment only after allergic diseases occur is changed. It can regulate human camp/cGMP and IgE, improve human immunity and correct allergic physique to inhibit and prevent effectively from the incidence of allergic diseases.
3. This pharmaceutical composition or extract of this invention have dual effects, that is, anti-histamine and inhibitors of allergic reaction mediums.
4. Besides the preventive and resistant functions of Type I Allergy, This pharmaceutical composition or extract of this invention can also increase immunity of physiques and strengthen human resistance to diseases.
5. For this pharmaceutical composition or extract of this invention, it is not only examined with human and animal tests, but also proven that it has prophylactic and anti-allergic effects. And the structure, contents and mechanism of its main function factors (cAMP of *Fructus Jujubae*, glycoside of *Radix scutellariae*, licorice acid) are also clarified.
6. This pharmaceutical composition or extract of this invention need not to be decocted. It is easy to transport and take it. They comply with the "Regulations of Health Law of the People's Republic of China".
7. This pharmaceutical composition or extract of this invention has potential values to develop series of products (health food and medicaments).

The present pharmaceutical composition or extract of this invention can be applied in the following area.

1. This product can be used as health food to regulate immune functions, correcting human allergic physique, inhibiting and preventing allergic reactions.
2. This product can be used as a medicament to cure Type I Allergy.
3. On the basis of this product, the series of anti-allergic medicaments can be explored and developed to cure allergic rhinitis, allergic asthma and allergic dermatitis and the like.

BRIEF DESCRIPTION OF DRAWING

In FIG. 1, the process flow diagram of this invention method is shown.

DETAILED DESCRIPTION OF THE INVENTION

The present invention is further described as follows in combination with appended FIGURE and examples.

EXAMPLE 1

300 g *Fructus Jujubae* was infiltrated into twofold amount of warm alcohol solution, two times, to get Fructus Jujubae extract. The warm temperature of infiltration is well known by the person skilled in the arts. And its pH value should be kept at 3.75. The extract liquid obtained from two warm infiltrations was put together. After subsiding for a while, it was filtered with a plate frame. The filtered extract was treated with the fractional absorption of macro-porous resin method that is well known by the person skilled in the arts to eliminate sugar. Then, the elution liquid should be combined, enriched and vacuumed in a vacuum dryer. The 42 g dry extract of *Fructus Jujubae* was obtained.

Grind 60 g ginger was squeezed to have ginger juice first. Then twofold amount of about 90 Degree centigrade hot water was added in the ginger residue and stirring it evenly. Said residue was squeezed again. The operation to squeeze was repeated four times. The ginger juice obtained was combined and filtered with a plate frame filter. The filtered ginger juice was stored for future use.

40 g green tea was infiltrated into boiled water and then extracted it five times. Add fivefold amount of water was added for the first time. From the second time to the fifth time, hot water was added until the water level is even with green tea. Each Infiltration and extraction lasted at least 10 minutes. The extracted solution was combined and filtered with a plate frame filter. The filtered juice was kept for future use.

120 g *Radix Astragali*, 80 g *Radix glycyrrhizae* and 60 g *Ramulus cinnamomi* were mixed and decocted together. Volatile oil of these three herbs was collected and extract was filtered with a plate frame filter. The mixed extract solution was obtained.

The mixed extract solution was obtained in the above-mentioned steps was mixed and concentrated. Then add the extract liquid of ginger was added and enriched continuously until thick paste was obtained, which has the relative density of 1.1/80° C. Then, the paste was vacuumed into a dry extract of 85.8 g.

The dry extract obtained in the above-mentioned steps was mixed and grinded with the obtained dry extract of *Fructus Jujubae*. So the extract of this invention was obtained.

EXAMPLE 2

600 g *Fructus Jujubae* was infiltrated into twofold amount of warm alcohol solution. The warm temperature of infiltration is well known by person skilled in the arts. And its pH value should be kept at 3.9. Said *Fructus Jujubae* was added six-fold 80 Degree centigrade hot water to extract for about 80 minutes. Then the residue was infiltrated and extracted in twofold 80 Degree centigrade hot water for about 20 minutes. The extract liquid obtained from the two infiltrations was combined together. After subsiding for a while, the liquid was filtered with a plate frame. The filtered liquid was treated with the fractional absorption of macro-porous resin method that is well known by the person skilled in the arts in order to eliminate sugar in it. Then, the elution liquid should be combined, enriched and vacuumed in a vacuum dryer. Finally 90 g dry extract of *Fructus Jujubae* was obtained.

120 g ginger was grinded and squeezed to obtain ginger juice at first. Then 2.5-fold amount of water was added in the ginger residue and stirring it evenly. Then said residue was squeezed again. The operation to squeeze the residue was repeated three times. The ginger juice obtained was combined and filtered with a plate frame filter. The filtered juice was kept for future use.

80 g green tea was infiltrated into boiled water and then extracted four times. Fivefold amount of about 100 Degree Centigrade hot water was added for the first time. From the second time to the forth time, add water until the water level was even with green tea. Green tea was Infiltrated and extracted every time for 10 minutes. The infiltrated liquid was put together and filtered with a plate frame filter. The filtered juice was stored for future use.

550 g Radix Astragali, 150 g *Radix glycyrrhizae* and 120 g *Ramulus cinnamomi* were mixed and decocted together. Volatile oil of these three herbs was collected and extract was filtered with a plate frame filter. The mixed extract solution was obtained.

The mixed extract solution was obtained in the above-mentioned steps was mixed and concentrated. Then add the extract liquid of ginger was added and enriched continuously until thick paste was obtained, which has the relative density of 1.4/85° C. Then, the paste was vacuumed into a dry extract of 210.6 g.

210.6 g dry extract obtained in the above-mentioned steps was mixed and grinded with the obtained dry extract of *Fructus Jujubae*. The extract of this invention was obtained.

EXAMPLE 3

The procedure of method described in Example 1 was repeated except that 100 g common peony root, the root of herbaceous peony (*Radix Paeoniae Alba*) and 100 g Baikal skullcap root (*Radix scutellariae*) were added when *Radix Astragali, Radix glycyrrhizae* and *Ramulus cinnamomi* were mixed and decocted.

EXAMPLE 4

The procedure of method described in Example 1 was repeated except that 150 g root of common peony root is added when *Radix Astragali, Radix glycyrrhizae* and *Ramulus cinnamomi* were mixed and decocted. The above-mentioned extract can be used as food replenishment or health food of human. The common daily dose is 2.5~6 g of human.

EXAMPLE 5

500 g *Fructus Jujubae*, 300 g *Radix glycyrrhizae* and 100 g *Ramulus cinnamomi* 80 g Ginger and 60 g Green tea were directly grinded into fine powder with the method that is well known by the person skilled in the arts. Then said fine powder was put into capsules or medicine bags such tea bag. It can be used as health food or health tea.

EXAMPLE 6

The dry extract obtained in Example 4 was grinded into powder. In accordance with the method that is well known by the person skilled in the arts, some specified amount of additives was added such as starch, milk sugar, aluminum hydrate, ethyloic sodium starch, silica gel micro-powder, magnesium stearate. The all substances were admixed evenly and compressed to form tablets with cover or transparent film that can be dissolved in stomach.

EXPERIMENTAL EXAMPLE 1

Research of anti-allergic pharmacodynamics of the pharmaceutical composition of the present invention

[Experimental Animal]

Wistar male rats with body weight of 100~120 g were used, which were provided by the Experimental Animal Center of the Chinese Academy of Medical Sciences.

[Experimental Medicament]

1. Tablets of this pharmaceutical composition obtained from Example 1 of this invention. It was made into a suspension with 0.5%CMC-Na.
2. Positive contrast medicament: disodium chromoglycate (produced by Shanghai Pharmaceutical Factory No. 5). It is dissolved with normal saline when it is used.

[Experimental Method]

After the rats were divided in groups at random, they were lavaged and dosed with the above-mentioned pharmaceutical composition of this invention according to 6 g/Kg and 3 g/Kg, once a day, continuously for 10 days. After hair on their backs of all groups of animals was removed, said animals were sensitized for the first time with hypodermic injection with anti-trichosanthes serum. At the same time, the dosing groups took the pharmaceutical composition according to 6 g/Kg, two hours before the second sensitization. The positive contrast groups were dosed with IV of disodium chromoglycate in accordance of 5 mg/Kg, one minute before the second sensitization was made. All groups of animals were given with IV of 1% EVANSLAN (including trichosanthes protein of 1 mg/ml) in accordance with 1 mg/Kg for the second sensitization. 20 minutes later, the animals were killed and their blue skins on their backs were cut off. Said skin were immersed in 7:3 acetone-normal saline solution over a night and then centrifuged. And 620 nm colorimetry is taken.

[Test Results]

See Table 1.

TABLE 1

| Group | Dose | Amount of animals | Dosing method | OD value (X ± SD) | Inhibition rate |
|---|---|---|---|---|---|
| Contrast group | — | 15 | — | 0.87 ± 0.25 | — |
| Positive contrast group | 5 mg/Kg | 10 | IV | 0.19 ± 0.11*** | 78.2 |
| Predosing group of the medicament of this invention | 6 g/Kg | 10 | PO | 0.42 ± 0.13*** | 51.7 |
|  | 3 g/Kg | 10 | PO | 0.62 ± 0.16** | 28.7 |
| Simultaneous Dosing group of the medicament of this invention | 6 g/Kg | 15 | PO | 0.59 ± 0.23** | 32.2 |

In comparison with the contrast group:
***P < 0.001
**P < 0.01

[Test Conclusion]

1. It has relatively good anti-allergic effects on the passive skin sensitization for the rats and relatively good dosageeffect relation when they are lavaged and dosed with the pharmaceutical composition of this invention according to 6~3 g/Kg, once a day, continuously for ten days.

2. It has relatively good anti-allergic effects on the passive skin sensitization for the rats when they are lavaged and dosed once with the pharmaceutical composition of this invention according to 6~3 g/Kg.

We claim:

1. A pharmaceutical composition for treating Type I Allergy, mainly comprising the following raw materials by weight ratio:

| | |
|---|---|
| Fructus Jujubae | 30 ~ 60 parts, |
| Radix Astragali | 12 ~ 55 parts, |
| Radix glycyrrhizae | 8 ~ 15 parts, |
| Ramulus cinnamomi | 6 ~ 12 parts, |
| Ginger | 6 ~ 12 parts, and |
| Green tea | 4 ~ 8 parts. |

2. A pharmaceutical composition according to claim 1, wherein said composition mainly comprises the following raw materials by weight ratio:

| | |
|---|---|
| Fructus Jujubae | 35 ~ 55 parts, |
| Radix Astragali | 15 ~ 50 parts, |
| Radix glycyrrhizae | 8 ~ 12 parts, |
| Ramulus cinnamomi | 6 ~ 10 parts, |
| Ginger | 6 ~ 10 parts, and |
| Green tea | 5 ~ 7 parts. |

3. A pharmaceutical composition according to claim 1, wherein said composition mainly comprises the following raw materials by weight ratio:

| | |
|---|---|
| Fructus Jujubae | 50 parts, |
| Radix Astragali | 30 parts, |
| Radix glycyrrhizae | 10 parts, |
| Ramulus cinnamomi | 8 parts, |
| Ginger | 8 parts, and |
| Green tea | 6 parts. |

4. A pharmaceutical composition according to claim 1, wherein said composition further comprises the following raw materials by weight ratio:

10~20 parts of Radix Paeoniae Alba and/or 10~20 parts of Radix scutellariae.

5. The pharmaceutical composition according to claim 1, wherein said composition further comprises pharmaceutically acceptable additives.

6. The pharmaceutical composition according to claim 1, wherein said composition is a medicament in a pharmaceutical product.

7. An extract for treating Type I Allergy obtained by the process comprising:

(a) Infiltrating 30~60 weight parts of Fructus Jujubae into a warm alcohol solution while keeping its pH value between 3.6~3.8 to obtain a Fructus Jujubae and alcohol mixture, extracting and filtering the Fructus Jujubae and alcohol mixture to obtain an extract solution, treating said extract solution by fractional absorption using a macroporous resin in order to eliminate sugar, and obtaining a dry extract of Fructus Jujubae by concentration;

(b) Squeezing 6~12 weight parts of ginger to obtain a ginger liquid and filtering the ginger liquid with a plate frame filter to obtain an extractive liquid of ginger;

(c) Infiltrating 4~8 weight parts of green tea into boiled water to obtain a green tea liquid and filtering the green tea liquid with a plate frame filter to obtain an extract liquid of green tea;

(d) Mixing and decocting 12~55 weight parts of Radix Astragali, 8~15 weight parts of Radix glycyrrhizae and 6~12 weight parts of Ramulus cinnamomi together to obtain a Radix Astragali, Radix glycyrrhizae and Ramulus cinnamomi mixture, filtering the Radix Astragali, Radix glycyrrhizae and Ramulus cinnamomi mixture to obtain a mixed extract liquid;

(e) Mixing and concentrating the mixed extract liquid obtained in step (d) with the extract liquid of green tea, then adding the extract liquid of ginger and concentrating the mixture until the mixture reaches a relative density of 1.1~1.4/80 at about 85° C. to obtain a thick paste and concentrating said paste into a dry extract; and (f) Grinding and mixing the dry extract obtained in step (e) with the dry extract of Fructus Jujubae obtained in step (a) to obtain an extract.

8. The extract according to claim 7, wherein said extract is prepared by extraction of the following raw materials by weight ratio:

| | |
|---|---|
| Fructus Jujubae | 35 ~ 55 parts, |
| Radix Astragali | 15 ~ 50 parts, |
| Radix glycyrrhizae | 8 ~ 12 parts, |
| Ramulus cinnamomi | 6 ~ 10 parts, |
| Ginger | 6 ~ 10 parts, |
| Green tea | 5 ~ 7 parts. |

9. The extract according to claim 7, wherein said extract is prepared by extraction of the following raw materials by weight ratio:

| | |
|---|---|
| Fructus Jujubae | 50 parts, |
| Radix Astragali | 30 parts, |
| Radix glycyrrhizae | 10 parts, |
| Ramulus cinnamomi | 8 parts, |
| Ginger | 8 parts, and |
| Green tea | 6 parts. |

10. The extract according to claim 7, further comprising 10~20 weight parts of Radix Paeoniae Alba and/or 10~20 weight parts of Radix scutellariae.

11. The extract according to claim 7, wherein said extract is a medicament in a pharmaceutical product.

12. The extract according to claim 7, wherein said extract further comprises pharmaceutically acceptable additives.

13. The method according to claim 12, wherein pharmaceutically acceptable additives are added into said extract.

14. The method according to claim 12, wherein the extract is processed into powder or tablet form.

15. The pharmaceutical composition according to claim 1, wherein the pharmaceutical composition is used to produce a health food product.

16. The pharmaceutical composition according to claim 1, wherein the pharmaceutical composition is used to produce an immune regulator.

17. The pharmaceutical composition according to claim 1, wherein the pharmaceutical composition is used to produce anti-allergic medicaments.

18. A method of making a composition for treating a Type I Allergy mainly comprising:
- (a) Infiltrating 30~60 weight parts of Fructus Jujubae into a warm alcohol solution while keeping its pH value between 3.6~3.8 to obtain a Fructus Jujubae and alcohol mixture, extracting and filtering the Fructus Jujubae and alcohol mixture to obtain an extract solution, treating said extract solution by fractional absorption using a macroporous resin in order to eliminate sugar, and obtaining a dry extract of Fructus Jujubae by concentration;
- (b) Squeezing 6~12 weight parts of ginger to obtain a ginger liquid and filtering the ginger liquid with a plate frame filter to obtain an extractive liquid of ginger;
- (c) Infiltrating 4~8 weight parts of green tea into boiled water to obtain a green tea liquid and filtering the green tea liquid with a plate frame filter to obtain an extract liquid of green tea;
- (d) Mixing and decocting 12~55 weight parts of Radix Astragali, 8~15 weight parts of *Radix glycyrrhizae* and 6~12 weight parts of *Ramulus cinnamomi* together to obtain a Radix Astragali, *Radix glycyrrhizae* and *Ramulus cinnamomi* mixture, filtering the Radix Astragali, *Radix glycyrrhizae* and *Ramulus cinnamomi* mixture to obtain a mixed extract liquid;
- (e) Mixing and concentrating the mixed extract liquid obtained in step (d) with the extract liquid of green tea, then adding the extract liquid of ginger and concentrating the mixture until the mixture reaches a relative density of 1.1~1.4/80 at about 85° C. to obtain a thick paste and concentrating said paste into a dry extract; and
- (f) Grinding and mixing the dry extract obtained in step (e) with the dry extract of Fructus Jujubae obtained in step (a) to obtain an extract.

19. The method of claim 18, further comprising adding 10~20 weight parts of Radix Paeoniae Alba and/or 10~20 weight parts of *Radix scutellariae*.

* * * * *